United States Patent
Sivaraman et al.

(10) Patent No.: US 9,452,145 B2
(45) Date of Patent: *Sep. 27, 2016

(54) TRANSDERMAL DOSAGE FORM FOR LOW-MELTING POINT ACTIVE AGENT

(71) Applicant: MYLAN, INC., Morgantown, WV (US)

(72) Inventors: Arunprasad Sivaraman, Pittsburg, PA (US); Tyler D. Simmons, Morgantown, WV (US); Gregory T. Fieldson, Pittsburg, PA (US); Adam C. Sorensen, Morgantown, WV (US); Jeffrey E. Cortopassi, Pittsburg, PA (US)

(73) Assignee: Mylan Inc, Canonsburg, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/725,010

(22) Filed: May 29, 2015

(65) Prior Publication Data
US 2015/0258037 A1    Sep. 17, 2015

Related U.S. Application Data

(63) Continuation of application No. 13/731,284, filed on Dec. 31, 2012, now Pat. No. 9,072,682.

(51) Int. Cl.
*A61K 9/70* (2006.01)
*A61K 31/4458* (2006.01)

(52) U.S. Cl.
CPC ........... *A61K 9/7038* (2013.01); *A61K 9/7023* (2013.01); *A61K 9/7084* (2013.01); *A61K 31/4458* (2013.01)

(58) Field of Classification Search
None
See application file for complete search history.

(56) References Cited

U.S. PATENT DOCUMENTS

| | | |
|---|---|---|
| 4,559,222 A | 12/1985 | Enscore et al. |
| 4,623,346 A | 11/1986 | Von Bittera et al. |
| 4,983,759 A | 1/1991 | Inoue et al. |
| 5,273,757 A | 12/1993 | Jaeger et al. |
| 5,508,038 A | 4/1996 | Wang et al. |
| 5,571,530 A | 11/1996 | Nakano et al. |
| 5,601,839 A | 2/1997 | Quan |
| 5,656,286 A | 8/1997 | Miranda et al. |
| 5,834,010 A | 11/1998 | Quan |
| 5,879,701 A | 3/1999 | Audett et al. |
| 5,948,433 A | 9/1999 | Burton et al. |
| 6,001,390 A | 12/1999 | Yum et al. |
| 6,348,210 B1 | 2/2002 | Gale |
| 6,555,130 B2 | 4/2003 | Wustling, et al. |
| 6,572,879 B1 | 6/2003 | Yum |
| 7,029,693 B2 | 4/2006 | Hori et al. |
| 7,718,188 B2 | 5/2010 | Ito et al. |
| 2007/0053968 A1 | 3/2007 | Tatapudy et al. |
| 2009/0155586 A1 | 6/2009 | Maitra |
| 2009/0286828 A1 | 11/2009 | Bozzoli et al. |
| 2011/0111013 A1 | 5/2011 | Salman et al. |
| 2011/0200663 A1 | 8/2011 | Hara et al. |
| 2012/0014885 A1 | 1/2012 | Collier et al. |
| 2012/0201891 A1 | 8/2012 | Cottrell et al. |

FOREIGN PATENT DOCUMENTS

WO    2011011318    1/2007

OTHER PUBLICATIONS

"Cabot, Fumed Silica and Fumed Alumina in Coatings Applications, Brochure (Apr. 28, 2008), accessed on", accessed online [http://www.cabot-corp.com/wcm/download/en-Us/fs/FS%20&%20FA%20in%20Coatings%20086769-eng.pdf] viewed on Jun. 9, 2014.
"International Search Report for PCT/US2013/076177 dated Jun. 6, 2014".
"Novartis Consumer Health", Transdermal Scop, 2006.
Tanner, et al., "Delivering drugs by the transdermal route: review and comment", Skin Research and Technology, 2008, 14(3), 249-260.

*Primary Examiner* — Susan Tran

(57) ABSTRACT

A drug-containing patch allows transdermal administration of a drug. The patch features a hydrophobic reservoir containing the drug, where the reservoir has a first surface and a second surface. A drug-impermeable backing overlies the first surface of the reservoir. A release sheet may overlie the second surface of the reservoir. The hydrophobic reservoir contains a drug and a hydrophobic matrix, where the hydrophobic matrix includes a hydrophobic filler in an amount which is effective to adsorb said drug; and a mixture of polyisobutylene and mineral oil. The hydrophobic matrix may contain hydrophobic colloidal silica as the hydrophobic filler. The hydrophobic reservoir layer may serve as a skin-contacting adhesive layer. Alternatively, a release-controlling adhesive layer may serve as the skin-contacting adhesive layer. The release-controlling adhesive layer may contain hydrophobic colloidal silica and a mixture of polyisobutylene and mineral oil.

25 Claims, No Drawings

TRANSDERMAL DOSAGE FORM FOR LOW-MELTING POINT ACTIVE AGENT

CROSS-REFERENCE TO RELATED APPLICATIONS

This application is a continuation of parent U.S. application Ser. No. 13/731,284 filed on Dec. 31, 2012. The entire disclosure of the prior application is hereby incorporated by reference in its entirety.

BACKGROUND

1. Field of the Invention

The current disclosure is directed to pharmaceutical preparations, particularly pharmaceutical preparations for manufacturing transdermal patches.

2. Description of Related Art

"Drug-in-adhesive" transdermal systems contain a drug-containing adhesive polymer layer, a drug-impermeable backing layer overlying one side of the adhesive layer, and a release layer, such as a silicone-coated paper layer, overlying the other side of the adhesive layer. Generally, in "drug-in-adhesive" transdermal systems, the adhesive polymer forms an outer or continuous phase. Various pharmacologically inactive ingredients, such as fillers or plasticizers, may be dissolved or dispersed in the polymeric matrix. Suitable adhesive polymers may include hydrophobic polymers, such as polyisobutylenes or (meth)acrylate ester polymers. The adhesive polymers, together with fillers, plasticizers, and other pharmacologically inactive ingredients, make up an adhesive hydrophobic matrix.

The pharmacologically active ingredients can be either dissolved or dispersed in the hydrophobic matrix. The solubility and the physical properties of the active pharmaceutical ingredient are of great importance in influencing the physical as well as the drug delivery performance of the transdermal system.

Many active pharmaceutical ingredients are able to undergo changes in their physical form during processing, i.e., from one polymorph to another or from solid to liquid. Such changes in physical form can give rise to several issues during processing or manufacturing. These include issues of crystallization or re-crystallization. In some cases, exposure to high temperatures or pressures during processing can lead to changes in the physical form of the active pharmaceutical ingredient. For example, a crystalline drug with a low melting point may be added to an adhesive composition which is then subjected to further processing. The adhesive composition may be subjected to heat or pressure during an extrusion process to form an adhesive layer, causing the drug to melt. Upon cooling of the adhesive composition after extrusion, the drug may solidify in an amorphous form, or in a crystalline polymorphic form which is different from its original form. In other cases, the drug may form an oil which is dispersed through the adhesive matrix.

Such changes in the physical form of the drug can affect the transdermal system as a whole. For example, if the active pharmaceutical ingredient has a low melting point and converts from its solid state to an oil state during processing, the oil state of the active ingredient can plasticize the adhesive matrix. Plasticizing the adhesive matrix can in turn cause delamination of the adhesive matrix from the drug-impermeable backing or from the release layer. Also, plasticizing the adhesive matrix can cause "cold flow," defined as distortion, deformation, or dimensional change at normal temperatures during storage conditions.

Additionally, if the active pharmaceutical ingredient is in oil form and is not sufficiently adsorbed in the adhesive matrix, or adsorbed by an excipient in the matrix, the oil can diffuse through the matrix and can cause film deposition or deposition of oil at the interface between the adhesive and the release liner interface. Diffusion of an oil through the adhesive matrix can also cause delamination and cold flow issues during storage.

Additionally, an adhesive layer may serve as a rate-limiting layer to control diffusion of oily drugs and other plasticizing agents from the drug reservoir to the interface between the reservoir and the backing.

There are known US marketed drug-in-adhesive transdermal products which contain a combination of polyisobutylene, mineral oil and colloidal silica as a transdermal matrix containing a drug such as scopolamine, clonidine or SALONPAS®. It has been claimed that the colloidal silica increases the viscosity in these products. It has also been claimed that the colloidal silica increases the permeability of the matrix, especially in transdermal products containing scopolamine or clonidine.

The present disclosure describes various embodiments, but is not intended to be exhaustive or limiting of the possible advantages that can be realized. Thus, the various embodiments are not intended to limit the scope of the invention. Accordingly, the present invention resides in the novel methods, arrangements, combinations, and improvements herein shown and described in various embodiments.

SUMMARY

In light of the present need for improved transdermal dosage forms for low-melting or highly diffusible drugs, a brief summary of various exemplary embodiments is presented. Some simplifications and omissions may be made in the following summary, which is intended to highlight and introduce some aspects of the various exemplary embodiments, but not to limit the scope of the invention. Detailed descriptions of a preferred exemplary embodiment adequate to allow those of ordinary skill in the art to make and use the inventive concepts will follow in later sections.

In a broad perspective, the transdermal systems disclosed herein include excipients which can substantially adsorb the drug molecules to overcome the deposition of oil or film formation at the adhesive-release liner interface or at the adhesive-backing layer interface. In certain embodiments, drug-in-adhesive transdermal systems can use silica particles as excipients to adsorb drug particles. In various embodiments, drug-in-adhesive transdermal systems can use hydrophobic excipients, including hydrophobic colloidal silica, to adsorb particles of hydrophobic drugs. In various embodiments, drug-in-adhesive transdermal systems can use more hydrophilic excipients, including conventional colloidal silica, to adsorb particles of hydrophilic drugs. Combinations of excipients may be used.

In various embodiments, the excipient is hydrophobic colloidal silica. Transdermal patches can be constructed with different levels of hydrophobic colloidal silica material by which the physical performance as well as the drug delivery performance of the patch can be altered. Transdermal compositions may include drug reservoir layers comprising polyisobutylene (high and low molecular weight), mineral oil, hydrophobic colloidal silica and the active pharmaceutical ingredient. Additionally, this composition involves a dependency between the choice of the level of hydrophobic colloidal silica material and the physical performance of the transdermal patch. In various embodiments, the colloidal silica is Aerosil® R972 Pharma, which has a specific surface area of between 90 and 130 m²/g.

In a first aspect, the current application is directed to laminating an adhesive layer to a drug reservoir layer to produce a transdermal system. In various embodiments, the rate of drug delivery can be controlled by the adhesive layer. Also, the current application is directed to a process by which the lamination of the adhesive layer to the drug reservoir layer can improve the physical performance of the transdermal system. The current specification also pertains to a transdermal composition which contains polyisobutylene (high and low molecular weight), mineral oil, hydrophobic colloidal silica and the active pharmaceutical ingredient in the drug reservoir layer and polyisobutylene (high and low molecular weight), mineral oil, and hydrophobic colloidal silica in the adhesive layer, also referred to as the skin contact layer.

The current disclosure relates to a patch for transdermal administration of a drug, comprising a hydrophobic reservoir containing the drug, where the reservoir has a first surface and a second surface. In various embodiments, a backing overlies the first surface, where the backing is impermeable to the drug. In certain embodiments, the hydrophobic reservoir layer is the outermost layer of the patch, and serves as a skin-contacting adhesive layer. In some embodiments, a release sheet overlies the second surface of the reservoir.

In various embodiments, the hydrophobic reservoir contains a drug and a hydrophobic matrix, where the hydrophobic matrix contains a hydrophobic filler in an amount which is effective to adsorb said drug; and a mixture of polyisobutylene and mineral oil. In various embodiments, the polyisobutylene and mineral oil are used in a weight ratio of mineral oil to polyisobutylene of at least about 0.05:1, at least about 0.25:1, or at least about 0.30:1. In various embodiments, the polyisobutylene and mineral oil are used in a weight ratio of mineral oil to polyisobutylene of up to about 1:1, up to about 0.60:1, or up to about 0.50:1. In various non-limiting embodiments, the weight ratio of mineral oil to polyisobutylene may be between about 0.05:1 and about 1:1. In various non-limiting embodiments, the weight ratio of mineral oil to polyisobutylene may be between about 0.25:1 and about 0.60:1. In various non-limiting embodiments, the weight ratio of mineral oil to polyisobutylene may be between about 0.30:1 and about 0.50:1. The hydrophobic matrix may contain from 6% to 30% by weight of the reservoir of hydrophobic colloidal silica as a hydrophobic filler. In various embodiments, the drug and the hydrophobic filler may be present in a weight ratio of between about 2:1 and about 0.9:1.

In various embodiments, the patch for transdermal drug administration comprises a hydrophobic reservoir containing the drug (the drug reservoir layer), where the reservoir has a first surface and a second surface, and a release-controlling adhesive layer in contact with said second surface of the reservoir. A drug-impermeable backing overlies the first surface. In certain embodiments, the release-controlling adhesive layer is the outermost layer of the patch. In some embodiments, a release sheet overlies the second surface of the reservoir, with the release-controlling adhesive layer being between the reservoir and the release sheet.

In various embodiments, the patch includes a release-controlling adhesive layer laminated to the drug reservoir layer, where the release-controlling adhesive layer comprises from 0.5% to 5% by weight of said release-controlling adhesive layer of hydrophobic colloidal silica; and a mixture of polyisobutylene and mineral oil in a weight ratio of polyisobutylene to mineral oil of between about 1:1 and about 4:1. The release-controlling adhesive layer contains a smaller amount of hydrophobic colloidal silica than the drug reservoir layer. In various embodiments, the hydrophobic matrix in the drug reservoir layer of the patch comprises from 8% to 20% by weight of the drug reservoir layer of hydrophobic colloidal silica; and the release-controlling adhesive layer comprises from 0.5% to 5% by weight of the release-controlling adhesive layer of hydrophobic colloidal silica. The hydrophobic colloidal silica may have a particle size of between 30 nm and 150 nm, although other sizes are also suitable. The hydrophobic silica may be colloidal silica which has been treated with a silane of formula I:

$$R_{(4-n)}SiX_n \qquad \qquad I$$

where R is a C1 to C20 alkyl or aromatic group, X is a hydrolysable group, and n is 1, 2, or 3. In various embodiments, X is —OH, —O₂CR¹, —Cl, —Br, —I, —COR¹, —NHR¹, or —NR¹₂, where R¹ is a C1 to C20 alkyl or aromatic group.

In various embodiments, the hydrophobic reservoir in the patch contains a low-melting drug, e.g., a drug having a melting point of between 20° C. and 150° C., or between 20° C. and 80° C. Suitable low-melting drugs include methylphenidate, ibuprofen, clonidine, or scopolamine. In various embodiments, the hydrophobic reservoir in the patch contains a hydrophobic drug which is able to diffuse through the hydrophobic matrix, where the diffusible hydrophobic drug may or may not be a low-melting drug. In various embodiments, the hydrophobic drug is capable of adsorbing to the surface of a hydrophobic filler or adsorbent, such as hydrophilic colloidal silica.

DETAILED DESCRIPTION OF VARIOUS DISCLOSED EMBODIMENTS

This disclosure describes a process by which, in a transdermal system, an adhesive layer can be laminated to a drug reservoir layer. The resulting transdermal system allows the rate of drug delivery to be controlled. Also, this disclosure pertains to a process by which lamination of an adhesive layer with varied thickness to a drug reservoir layer can improve the physical performance of the transdermal system. The invention also pertains to a transdermal composition which contains polyisobutylene (high and/or low molecular weight polyisobutylene), mineral oil, hydrophobic colloidal silica and an active pharmaceutical ingredient. The active pharmaceutical ingredient is included in a drug reservoir layer, where the drug reservoir layer contains a hydrophobic polymeric matrix containing polyisobutylene, which may be high molecular weight polyisobutylene, low molecular weight polyisobutylene, or a mixture thereof; mineral oil, and hydrophobic colloidal silica.

The polyisobutylene may be high molecular weight polyisobutylene, low molecular weight polyisobutylene, or a mixture thereof. The high molecular weight polyisobutylene may have an average molecular weight of 500,000 to 1.5 million, or from 750,000 to 1.2 million. The low molecular weight polyisobutylene may have an average molecular weight of 40,000 to 85,000. Suitable polyisobutylene adhesives include Oppanol B80 (a high molecular weight PIB), Oppanol B100 (a high molecular weight PIB), Oppanol B12 (a low molecular weight PIB), and Duro-Tak 87-613A (a mixture of high and low molecular weight PIBs). For adhesives using a mixture of high and low molecular weight PIBs, the ratio of high molecular weight to low molecular weight PIB may range from 0.5:1 to 1.5:1; 0.6:1 to 1.1:1; or about 0.8:1. The active pharmaceutical ingredient is included in a drug reservoir layer, where the drug reservoir layer contains a hydrophobic polymeric matrix containing polyisobutylene, which may be high molecular weight polyisobutylene, low molecular weight polyisobutylene, or a mixture thereof; mineral oil, and hydrophobic colloidal silica.

Generally, in "drug-in-adhesive" transdermal systems, the adhesive polymer is considered as the outer or continuous phase. The pharmacologically inactive ingredients are dissolved or dispersed in the adhesive polymer and the pharmacologically active ingredients can be either dissolved or dispersed in the adhesive polymer as well. The solubility and the physical properties of the active pharmaceutical ingredient are of great importance in influencing the physical as well as the drug delivery performance of the transdermal system.

During processing or manufacturing, the active pharmaceutical ingredient may undergo changes in its physical state. These changes include crystallization/re-crystallization and/or conversion of a drug having a defined physical form into a different physical form. Such changes in the drug can in turn affect the transdermal system as a whole. For example, if the active pharmaceutical ingredient has a low melting point and is heated above its melting point during processing, the active pharmaceutical ingredient can be converted from a solid state to a liquid or oily state during processing. The liquid or oily form of the active pharmaceutical ingredient can plasticize the matrix and can cause delamination during the manufacturing process. Further, the oily or liquid active pharmaceutical ingredient can diffuse through the matrix of the transdermal system and can cause film deposition or deposition of oil at the adhesive-release liner interface.

To overcome these problems, an excipient may be added to the matrix. A suitable excipient should have a significant adsorption capacity for the active ingredient. Other factors include the interaction of the excipient with the active pharmaceutical ingredient, as well as the introduction of impurities by the excipient. Optimization of these factors is often performed in the manufacture of a physically acceptable transdermal system. Failure to properly address these factors can cause inferior performance of a transdermal system, even though other aspects of the formulation are thoroughly optimized.

For example, some drugs are subject to degradation by hydrolysis. The extent of drug degradation by hydrolysis is mainly determined by the moisture present in the carrier in addition to other moisture introducing factors. In a transdermal system containing a hydrophobic matrix such as polyisobutylene/mineral oil matrix, little moisture is contributed by the hydrocarbon polymers and oils. However, colloidal silica is hydrophilic, and contains water adsorbed on the silica particles. The amount of moisture present or adsorbed on the silica particles can directly influence the stability of the adsorbed drug. Accordingly, colloidal silica may not be the ideal excipient for adsorbing a drug which is subject to hydrolysis, as the drug may be bound in close proximity to adsorbed water. Further, colloidal silica has a hydrophilic surface which may repel hydrophobic drugs. To address these issues, a hydrophobic adsorbent may be used with a hydrophobic drug or a drug which undergoes hydrolysis readily. Hydrophobic colloidal silica is a possible example of a hydrophobic adsorbent.

Colloidal silicon dioxide, also known as colloidal silica, is an excipient approved by the Food and Drug Administration (FDA) as a GRAS (Generally Regarded As Safe) material for use in topical pharmaceutical preparations. Because of its valuable properties like large surface area, low density and small particle size, it is well recognized as being capable of adsorbing some active pharmaceutical ingredients. The adsorptive nature of the silica particles is a significant factor contributing to their use as carriers in some pharmaceutical preparations.

In certain embodiments, the transdermal system contains a single-layer adhesive system. The reservoir layer is an adhesive material and has two major surfaces. A drug-impermeable backing layer is laminated to one major surface of the reservoir layer; and a release liner, such as a silicone-coated paper layer, is releasably laminated to the other major surface of the reservoir layer. The release liner may be peeled off of the reservoir layer to reveal an adhesive surface of the reservoir layer. The exposed adhesive surface may then be adhered to a skin surface, allowing the drug to diffuse through the hydrophobic matrix of the reservoir matrix to the skin surface. In various embodiments, the reservoir layer contains a mixture of polyisobutylene and mineral oil in a weight ratio of mineral oil to polyisobutylene of between about 0.05:1 and about 1:1. In various non-limiting embodiments, the weight ratio of mineral oil to polyisobutylene may be between about 0.25:1 and about 0.60:1. In various non-limiting embodiments, the weight ratio of mineral oil to polyisobutylene may be between about 0.30:1 and about 0.50:1. The reservoir layer may contain from 6% to 30% by weight of the reservoir of hydrophobic colloidal silica as a hydrophobic filler.

In certain embodiments, the reservoir layer is laminated to an adhesive layer to produce a bilayer adhesive system. The adhesive layer may also be referred to as the skin contact layer or as the skin-contacting adhesive layer. In embodiments containing both a reservoir layer and a skin-contacting adhesive layer, the reservoir layer and the skin-contacting adhesive layer are laminated together. In various embodiments, the reservoir layer contains from about 8% to about 30% by weight of the active ingredient; a drug-adsorbing excipient, such as hydrophobic colloidal silica; and a mixture of polyisobutylene and mineral oil in a weight ratio of said polyisobutylene to said mineral oil of between about 1:1 and about 4:1. In various embodiments, the reservoir layer contains from about 8% to about 30%, or about 8% to about 20%, by weight of the reservoir layer of hydrophobic colloidal silica as a drug-adsorbing excipient. The skin-contacting adhesive layer contains from about 0.5% to about 5%, or about 1% to about 3%, by weight of the release-controlling adhesive layer of hydrophobic colloidal silica; and a mixture of polyisobutylene and mineral oil in a weight ratio of said polyisobutylene to said mineral oil of between about 1:1 and about 4:1. In certain embodiments, the skin-contacting adhesive layer is free of any active ingredients.

Suitable excipients to be added to a drug reservoir layer which may be used to adsorb drugs include, in amounts by weight of the reservoir layer:

hydrophobic colloidal silica in an amount of about 8% to about 30%;

a combination of hydrophobic colloidal silica in an amount of about 1% to about 3% and titania (titanium dioxide) in an amount of about 2%;

neusilin (magnesium aluminometasilicate) in an amount of about 2% to about 5%;

a combination of neusilin (magnesium aluminometasilicate) in an amount of about 2% to about 5% and at least one of magnesium stearate in an amount of about 2% to about 5%, polyethoxylated castor oil in an amount of about 2% to about 5%, and a mixture thereof;

colloidal silica or dried colloidal silica in an amount of about 1% to about 10%;

a combination of colloidal silica in an amount of about 1% to about 3% and neusilin in an amount of about 2%, magnesium stearate in an amount of about 1% to about 3%, disodium hydrogen phosphate in an amount of about 2% to about 5%, polyethoxylated castor oil in an amount of about 2% to about 5%, or a mixture thereof;

disodium hydrogen phosphate in an amount of about 2% to about 5%;

anhydrous calcium phosphate dibasic in an amount of from 5% to about 10%;

a combination of anhydrous calcium phosphate dibasic in an amount of from 5% to about 10% and polyethoxylated castor oil in an amount of about 2% to about 5%;

polyethoxylated castor oil in an amount of about 2% to about 5%;

magnesium stearate in an amount of about 2% to about 5%;

clays such as kaolin in an amount of about 5% by weight;
up to 1% by weight of alpha-tocopherol; and
from about 5% to about 20% Eudragit EPO, a cationic copolymer based on dimethylaminoethyl methacrylate, butyl methacrylate, and methyl methacrylate.

In certain embodiments, polymers such as polyethylene glycol, polyvinyl pyrrolidone or hydroxypropyl methylcellulose may be used as an adsorbent in an amount of between about 3% and 7% by weight.

In various embodiments, hydrophobic excipients may be used to preferentially adsorb hydrophobic drugs. Hydrophilic excipients may be used to adsorb less hydrophobic drugs.

Suitable hydrophobic excipients for use with hydrophobic drugs include hydrophobic colloidal silica; a combination of hydrophobic colloidal silica and titania; polyethoxylated castor oil; and magnesium stearate.

Various embodiments disclosed herein use hydrophobic colloidal silica as a hydrophobic excipient. Conventional colloidal silica has a hydrophilic surface with silanol groups. Although hydrophilic colloidal silica has been used in transdermal systems, hydrophilic colloidal silica is a poor adsorbent for hydrophobic drugs, such as methylphenidate. To address this issue, the transdermal system disclosed herein uses a hydrophobic colloidal silica as a filler and adsorbent. In various embodiments, the hydrophobic colloidal silica used as an adsorbent may be a chemically modified colloidal silica. In some embodiments, the colloidal silica has been treated with a hydrolysable silane of formula I:

$$R_{(4-n)}SiX_n \qquad I$$

where R is a C1 to C20 alkyl or aromatic group, X is a hydrolysable group, and n is 1, 2, or 3. In various embodiments, X is —OH, —O$_2$CR$^1$, —Cl, —Br, —I, —OR$^1$, —COR$^1$, —NHR$^1$, or —NR$^1{}_2$, where R$^1$ is a C1 to C20 alkyl or aromatic group. The hydrolysable silane is attached to the colloidal silica by a condensation reaction between the —SiX$_n$ group on the silane and silanol groups on the colloidal silica, replacing hydrophilic silanol groups on the silica surface with hydrophobic alkyl groups.

Because of its excellent surface area, hydrophobic colloidal silica can effectively adsorb hydrophobic drugs and other hydrophobic ingredients. Also from a drug stability point of view in this process, the stability of the drug reservoir in the transdermal patch depends on the interaction between the hydrophobic colloidal silica and the drug. By using hydrophobic colloidal silica at a certain percentage (from about 6% to about 30%, preferably from about 8% to about 20% in the formulation) as an excipient, the diffusion of the active pharmaceutical ingredient through the matrix can be controlled during storage. Specifically, the hydrophobic drug and other hydrophobic ingredients adsorb to the hydrophobic surface of the silica particles. When at least a portion of the hydrophobic ingredients, i.e., from about 20% to about 100% of the hydrophobic ingredients, adsorb to the hydrophobic silica surface, this reduces or prevents free diffusion of the hydrophobic ingredients, including hydrophobic drugs, through the hydrophobic matrix. Reducing drug diffusion in this manner increases stability of the transdermal patch, as the drug does not diffuse to the surfaces of the hydrophobic reservoir layer. Thus, adsorption of the drug to the hydrophobic colloidal silica can be considered as a significant factor in controlling the diffusion of the drug molecules. In the absence of hydrophobic colloidal silica, the hydrophobic drug, particularly liquid or oily drugs, may diffuse through the hydrophobic matrix to the surfaces of the hydrophobic reservoir layer, establishing a layer of drug at the interface between the reservoir layer and adjacent layers. This can reduce adhesion between layers, leading to delamination of the layers of the transdermal system.

Hydrophobic colloidal silica is used in various exemplary embodiments due to its excellent physicochemical and physiological properties. Hydrophobic colloidal silica has a large specific surface area for drug deposition, as well as exhibiting strong adsorption to hydrophobic drugs. Uniform distribution of the drug molecules and the hydrophobic colloidal silica in the hydrophobic matrix of the drug reservoir can be ensured with a well optimized mixing strategy which allows the drug molecules to be uniformly distributed over the silica particles. However, the stability of the drug depends upon the impurities of the excipient as well as the absorbed moisture by the excipient.

Drug degradation by hydrolysis is mainly determined by the moisture present in the pharmacologically active and inactive ingredients or by the moisture present in the system. The amount of moisture present or adsorbed on the silica particles can directly influence the stability of the adsorbed drug.

The effect of drug-adhesive mixing in the presence of hydrophobic colloidal silica was studied. With a drug reservoir containing hydrophobic colloidal silica in an amount of between about 8% and 20%, physical issues faced during the manufacturing process and during accelerated stability storage conditions were resolved, allowing production of an acceptable transdermal system. With a drug reservoir containing hydrophobic colloidal silica in an amount of 5%, or with a reservoir in which hydrophobic colloidal silica was absent, these physical issues were not successfully resolved. Even with a physically acceptable transdermal system, controlling the drug delivery performance was a significant challenge.

This challenge was addressed by designing an adhesive layer with a composition similar to the drug reservoir layer, where the adhesive layer contains polyisobutylene (high and low molecular weight), mineral oil, and hydrophobic colloidal silica with varied percentages of each component.

The adhesive layer was laminated to a first major surface of the drug reservoir layer. By laminating the adhesive layer to the drug reservoir layer, which includes polyisobutylene, mineral oil, active pharmaceutical ingredient and hydrophobic colloidal silica, an acceptable controlled rate of drug delivery may be attained. A drug-impermeable backing layer was laminated to a second major surface of the reservoir layer.

In various embodiments, a protective layer covers the adhesive layer. In some embodiments, the protective layer is a release sheet, such as a silicone-coated paper sheet, laminated to a surface of the adhesive layer opposite the drug reservoir layer. In other embodiments, the drug-impermeable backing layer may include a release layer coated on the surface opposite the reservoir layer. The transdermal system is prepared in a form which may be stacked or rolled so that the release layer on the drug-impermeable backing layer protects the adhesive layer on an adjacent transdermal system.

In various embodiments, the adhesive layer contains no drug at the time of manufacturing. In some embodiments, the adhesive layer contains a drug in a low concentration which is less than the concentration of the drug in the adjacent reservoir layer. The adhesive layer may contain a low concentration of drug as a result of drug diffusion from the reservoir layer to the adhesive layer subsequent to manufacturing. Alternatively, the adhesive layer may be manufactured with a low concentration of drug in the adhesive layer and a high concentration of drug in the reservoir layer. The hydrophobic colloidal silica in the adhesive layer is present in an amount of between about 0.5% and about 5% by weight of the adhesive layer. In certain embodiments, the hydrophobic colloidal silica in the adhesive layer is present in an amount of between about 1% and about 3% by weight of the adhesive layer. The hydrophobic colloidal silica in the adhesive layer retards diffusion of a drug through the adhesive layer by adsorbing the drug. Since the concentration of drug in the adhesive layer is less than the concentration of drug in the reservoir layer, a smaller concentration of hydrophobic colloidal silica is required to adsorb drug in the adhesive layer than in the reservoir layer. The hydrophobic colloidal silica in the adhesive layer may be used to adsorb drug present in the adhesive layer at the time the transdermal system is manufactured, or to adsorb drug which diffuses into the adhesive layer from the reservoir layer after the transdermal system is manufactured.

Also, drug crystallization, which is a serious physical appearance issue in transdermal systems, was controlled by using an additional adhesive layer laminated to the reservoir layer. In addition, this bilayer approach resulted in improved tack compared to a monolayer approach and solved the problem of delamination.

Various embodiments disclosed herein relate to a process by which in a transdermal system, a mixture of a polyisobutylene adhesive, an adsorbent capable of adsorbing an active pharmaceutical, and mineral oil act as a drug reservoir for an active pharmaceutical ingredient of low melting point. In various embodiments, particularly embodiments in which the active pharmaceutical is hydrophobic or is easily hydrolyzed, the adsorbent is a hydrophobic adsorbent, such as hydrophobic colloidal silica. The active pharmaceutical ingredient of low melting point is a drug having a melting point of between about 20° C. and about 150° C., or between about 20° C. and about 80° C. In various embodiments, the drug of low melting point exists in a liquid or oil state at or slightly above room temperature, and may melt during storage. In various embodiments, the drug of low melting point has a melting point above room temperature, but less than temperatures experienced during processing. Accordingly, the drug can change its physical state from solid to liquid, and possibly even to gaseous form, depending upon the processing conditions or storage conditions. If the drug exists in liquid or oily form during manufacture or storage, the active ingredient may plasticize the hydrophobic matrix. Since the mineral oil already acts as a plasticizer, the combination of mineral oil and an oily drug can plasticize the reservoir matrix to the point that dimensional stability of the matrix is lost. The matrix may undergo cold flow during storage, allowing the matrix to expand in length or width to the point that the adhesive reservoir expands beyond the boundaries of the drug-impermeable backing layer.

Additionally, the presence of drug in the liquid form or in an oil form can allow the drug to diffuse the matrix as a non-solid material, and cause film formation or deposition of the liquid or oil at the reservoir-release liner interface or at the reservoir-backing layer interface. This can cause solidification and/or crystallization of the drug at the interface between layers, or formation of a liquid or oil drug layer at the interface between layers. The presence of solid or liquid drug at the interface between layers can reduce the area of direct contact between layers, and lead to reduced adhesion at the reservoir-release liner interface or at the reservoir-backing layer interface. In extreme cases, such reduced adhesion can cause delamination of layers during storage. Accordingly, the presence of drug in an oily or liquid form can lead to poor physical performance of the transdermal system, including delamination and loss of dimensional stability.

In various embodiments, the hydrophobic matrix for the reservoir layer may be made by mixing a polymer such as polyisobutylene, mineral oil, hydrophobic colloidal silica, and a drug under high shear conditions. In various embodiments, the hydrophobic matrix for the reservoir layer may be made by mixing polyisobutylene, mineral oil, hydrophobic colloidal silica, and a drug in a batch process high-shear rotor-stator mixer. In such a mixer, the rotor blades turn within a close tolerance stator. The small gap between the blades and the stator, coupled with high rotational speeds, allows for homogenization of polymer blends, e.g., polyisobutylene/mineral oil blends. The high-shear rotor-stator mixer also serves to break up silica agglomerates and uniformly disperse the hydrophobic colloidal silica and drug in the hydrophobic polyisobutylene matrix. After preparation of the hydrophobic matrix under high shear, the hydrophobic matrix polymer may be deposited on a drug-impermeable backing layer, and a release liner is then applied to the exposed surface of the hydrophobic matrix layer.

In various embodiments, the hydrophobic matrix for the reservoir layer may be made by mixing a polymer such as polyisobutylene, mineral oil, hydrophobic colloidal silica, and a drug in an extruder. In various embodiments, the hydrophobic matrix for the reservoir layer may be made by mixing polyisobutylene, mineral oil, hydrophobic colloidal silica, and a drug under elevated temperatures in an extruder, and extruding the resulting mixture to form a reservoir layer. The drug may be added to the mixture as a solid, which then melts when exposed to elevated temperatures in the extruder. Upon cooling, the drug may be dispersed in the reservoir matrix as an oil or as a liquid.

Uniform distribution of the drug molecules with the hydrophobic colloidal silica can only be ensured with a well-optimized mixing strategy. The drug molecules can be uniformly distributed over the hydrophobic colloidal silica particles. In various embodiments, hydrophobic colloidal silica and a hydrophobic drug can be mixed into a hydrophobic polymeric composition in an extruder. Mixing in the extruder homogeneously disperses the hydrophobic colloidal silica and the hydrophobic drug in the hydrophobic polymeric composition. Homogeneous dispersion of the hydrophobic colloidal silica and the drug in this manner allows the drug to adsorb to the hydrophobic colloidal silica. The resulting composition may be extruded as a hydrophobic matrix layer.

In various embodiments, the extruded hydrophobic matrix layer is deposited on a drug-impermeable backing layer, and a release liner is then applied to the exposed surface of the hydrophobic matrix layer. In some embodiments, the hydrophobic matrix layer and the hydrophilic backing layer are coextruded to form a laminate, and a release liner is then applied to an exposed surface of the hydrophobic matrix layer.

In various embodiments, the reservoir matrix is a combination of polyisobutylene and mineral oil. Hydrophobic silica material is homogeneously dispersed through the reservoir matrix. The hydrophobic silica material has a strong interaction with the oily or liquid hydrophobic active pharmaceutical ingredient dispersed in the matrix. More specifically, at least a portion of the oily or liquid hydrophobic active pharmaceutical is adsorbed to the hydrophobic silica material, thereby preventing or reducing diffusion of the active pharmaceutical through the hydrophobic matrix. Additionally, oily or liquid hydrophobic active pharmaceutical which has been adsorbed to the hydrophobic silica material behaves as a solid material and has a reduced tendency to plasticize the reservoir matrix. Accordingly, adsorption of an oily or liquid drug to hydrophobic colloidal silica, or to a similar adsorbent, reduces delamination and loss of dimensional stability in the resulting transdermal system.

To manufacture an acceptable transdermal system with an active pharmaceutical ingredient having low melting point, the polyisobutylene adhesive, hydrophobic colloidal silica and mineral oil combination was considered as a carrier for the dispersed/modified active ingredient in its oil state. The interaction of the polyisobutylene and the hydrophobic colloidal silica with the mineral oil was considered very significant in influencing the physical properties of the whole transdermal system. The silica materials can provide a physically acceptable transdermal system for an active ingredient which is in the oil state with the combination of polyisobutylene and mineral oil. Especially, the hydrophobic silica material can provide an acceptable transdermal system both physically and chemically. This fact is especially true if the active pharmaceutical ingredient is easily prone to hydrolytic degradation. While many materials are able to adsorb hydrophobic drugs, including colloidal silica, hydrophobic excipients such as hydrophobic colloidal silica have the advantage that they do not also adsorb water. Use of a hydrophilic excipient to adsorb a drug can result in adsorption of both the drug and water to the excipient surface, thereby increasing the likelihood of hydrolysis of the drug by the water. In some cases, the adsorbent actually catalyzes hydrolysis of the drug by the water. Since a hydrophobic excipient, such as hydrophobic colloidal silica, does not adsorb water, adsorption of a drug to a hydrophobic excipient does not increase the likelihood of hydrolysis of the drug.

Additionally, a hydrophilic excipient contains a significant amount of adsorbed water, while a hydrophobic excipient contains a much smaller amount of adsorbed water. Thus, use of a hydrophilic excipient introduces more water into the transdermal system than a hydrophobic excipient. Adding a hydrophilic excipient to a hydrophobic drug reservoir causes addition of water to the reservoir layer, thereby increasing the extent of drug hydrolysis. Adding a hydrophobic excipient to a hydrophobic drug reservoir does not add significant water to the reservoir layer, and therefore does not increase the extent of drug hydrolysis. Thus, the stability of the drug depends upon the adsorbed moisture on the excipient surface, as well as free moisture present in the system.

The drug degradation by hydrolysis is mainly determined by the moisture present in the pharmacologically active and inactive ingredients or by the moisture present in the system. The hydrophilic nature of the adhesive and the excipients as well as the amount of moisture present or adsorbed on the silica particles during the processing and storage conditions can directly influence the stability of the adsorbed drug.

Further, a layer of a release-controlling hydrophobic polymeric material may be present in between the hydrophobic reservoir matrix and the release liner. Upon removal of the release liner, the release-controlling hydrophobic polymeric material layer acts as a skin-contacting adhesive layer. In various embodiments, the hydrophobic reservoir matrix and the layer of a release-controlling hydrophobic polymeric material may be made of substantially the same polymeric material, or from different polymeric materials.

In various embodiments, both the hydrophobic reservoir matrix and the layer of a release-controlling hydrophobic polymeric material contain a combination of polyisobutylene and mineral oil in a weight ratio of mineral oil to polyisobutylene of between about 0.05:1 and about 1:1, preferably between about 0.25:1 and about 0.60:1, more preferably between about 0.30:1 and about 0.50:1. The hydrophobic reservoir matrix additionally contains a hydrophobic drug and from 8% to 20% by weight of a hydrophobic excipient capable of adsorbing the drug. The layer of the release-controlling hydrophobic polymeric material additionally contains from 0.5% to 5%, preferably 1% to 3%, by weight of a hydrophobic excipient capable of adsorbing the drug in the hydrophobic reservoir matrix. The layer of the release-controlling hydrophobic polymeric material may be manufactured without a drug, or including an amount of drug which is smaller than the amount of the drug in the hydrophobic reservoir matrix layer. In the event that the layer of the release-controlling hydrophobic polymeric material is manufactured without a drug, the layer of the release-controlling hydrophobic polymeric material may include a small amount of drug at the time of use due to diffusion of drug from the reservoir layer during storage.

The layer of the release-controlling hydrophobic polymeric material acts to control release of the drug from the reservoir layer both during storage and during use. The release-controlling hydrophobic polymeric material provides an additional layer of polymeric material through which the drug must diffuse to reach the release liner during storage, or to reach a skin surface during use of the transdermal system. Additionally, the release-controlling hydrophobic polymeric material contains hydrophobic colloidal silica, which acts to adsorb the drug as it diffuses through the release-controlling hydrophobic polymeric layer, thereby slowing diffusion of the drug through the release-controlling hydrophobic polymeric layer.

In various embodiments, the hydrophobic reservoir matrix layer and the release-controlling hydrophobic polymeric material may be separately extruded, and then laminated together. Alternatively, the hydrophobic reservoir matrix layer and the release-controlling hydrophobic polymeric material may be co-extruded to produce a laminate. The resulting laminate is deposited on a drug-impermeable backing layer so that an exposed surface of the reservoir matrix layer contacts the backing layer, and a release liner may then be applied to an exposed surface of the release-controlling hydrophobic polymeric material layer. In some embodiments, the release-controlling hydrophobic polymeric material, the hydrophobic matrix layer and the hydrophilic backing layer are coextruded to form a laminate with an exposed adhesive surface of the release-controlling layer. A release liner is then applied to an exposed surface of the release-controlling layer.

Examples of Transdermal Patches with Hydrophobic Matrix Layers Laminated to a Release Liner A series of transdermal patches was prepared, as shown in Table 1. Each transdermal patch included a hydrophobic matrix layer, a drug-impermeable backing laminated to one surface of the hydrophobic matrix layer, and a release liner laminated to the other surface of the hydrophobic matrix layer. The hydrophobic matrix layer contained methylphenidate as a hydrophobic drug in an amount of between 8% by weight and 20% by weight. In various examples, the hydrophobic matrix layer also contained a combination of mineral oil (MO) and polyisobutylene (PIB) as a polymeric matrix, in a weight ratio of MO:PIB of between about 0.09:1 and about 1.1:1.

In various comparative examples (identified in Table 1 as "Comp."), the hydrophobic matrix layer contained hydrophobic colloidal silica in an amount of between 0% by weight and 5% by weight. The comparative examples showed poor stability upon storage under accelerated storage conditions. After storage under accelerated storage conditions, the comparative examples showed evidence of dimensional change during storage, due to cold flow of the hydrophobic matrix layer. Additionally, the release layers on the comparative examples were removed after storage, and the exposed surfaces of the hydrophobic matrix layers were examined. In several cases, evidence of oily or liquid layers at the interfaces between the release layers and the hydrophobic matrix layers were observed. Additionally, some comparative examples showed crystallization of methylphenidate at the surfaces of the hydrophobic matrix layers. The comparative examples showed frequent evidence of release layer delamination, or premature delamination of the release layer. In short, with levels of hydrophobic colloidal silica of 5 wt. % or less, the physical and chemical properties of the transdermal system were poor.

In various working examples, the hydrophobic matrix layer contained hydrophobic colloidal silica in an amount of between 8% by weight and 30% by weight. The working examples showed good stability upon storage under accelerated storage conditions. After storage under accelerated storage conditions, the working examples showed little or no evidence of dimensional change during storage under accelerated storage conditions. Additionally, the working examples showed little increase in ease of release layer delamination, or premature delamination of the release layer, after storage under accelerated storage conditions. Finally, the release layers on the working examples were removed, and the exposed surfaces of the hydrophobic matrix layers were examined. Little or no evidence of oily or liquid layers at the interfaces between the release layers and the hydrophobic matrix layers was observed in most cases. Additionally, minimal crystallization of methylphenidate at the surfaces of the hydrophobic matrix layers was observed. Upon increasing the levels of hydrophobic colloidal silica in the hydrophobic matrix layer to between 8% by weight and 30% by weight, the physical and chemical properties of the transdermal system showed significant improvement, when compared to the comparative examples.

TABLE 1

Transdermal Methylphenidate Formulations

| Example Number | Drug (%) | HCS (%) | Mineral Oil (%) | Polybutadiene (%) | Results | MO:PIB Ratio |
|---|---|---|---|---|---|---|
| Comp. 1 | 20.00 | 3.00 | 20.00 | 57.00 | X | 0.35 |
| Comp. 2 | 20.00 | 1.00 | 20.00 | 59.00 | X | 0.34 |
| Comp. 3 | 20.00 | 1.00 | 40.00 | 39.00 | X | 1.03 |
| Comp. 4 | 20.00 | 3.00 | 40.00 | 37.00 | X | 1.08 |
| Comp. 5 | 20.00 | 2.50 | 20.00 | 57.50 | X | 0.35 |
| Comp. 6 | 16.00 | 3.00 | 27.00 | 54.00 | X | 0.50 |
| Comp. 7 | 13.00 | 3.00 | 28.00 | 56.00 | X | 0.50 |
| Comp. 8 | 16.00 | 3.00 | 20.00 | 61.00 | X | 0.33 |
| Comp. 9 | 10.00 | 1.00 | 29.67 | 59.33 | X | 0.50 |
| Comp. 10 | 16.00 | 1.00 | 27.67 | 55.33 | X | 0.50 |
| Comp. 11 | 16.00 | 3.00 | 27.00 | 54.00 | X | 0.50 |
| 1 | 20.00 | 10.00 | 20.00 | 50.00 | ○ | 0.40 |
| 2 | 16.00 | 9.00 | 25.00 | 50.00 | ○ | 0.50 |
| 3 | 18.00 | 10.00 | 24.00 | 48.00 | ○ | 0.50 |
| 4 | 14.00 | 20.00 | 22.00 | 44.00 | ○ | 0.50 |
| 5 | 18.00 | 20.00 | 20.67 | 41.33 | ○ | 0.50 |
| 6 | 18.00 | 20.00 | 5.00 | 57.00 | ○ | 0.087 |
| 7 | 18.00 | 20.00 | 10.00 | 52.00 | ○ | 0.19 |
| 8 | 18.00 | 20.00 | 17.33 | 44.67 | ○ | 0.39 |
| Comp. 12 | 20.00 | 0.00 | 20.00 | 60.00 | X | 0.33 |
| Comp. 13 | 20.00 | 0.00 | 40.00 | 40.00 | X | 1.00 |
| Comp. 14 | 20.00 | 5.00 | 40.00 | 35.00 | X | 1.14 |
| Comp. 15 | 8.00 | 0.00 | 30.65 | 61.35 | X | 0.50 |
| Comp. 16 | 16.00 | 0.00 | 28.00 | 56.00 | X | 0.50 |
| Comp. 17 | 16.00 | 5.00 | 26.33 | 52.67 | X | 0.50 |
| Comp. 18 | 10.00 | 5.00 | 28.33 | 56.67 | X | 0.50 |
| 9 | 20.00 | 20.00 | 16.00 | 44.00 | ○ | 0.36 |
| 10 | 20.00 | 10.00 | 18.67 | 51.33 | ○ | 0.36 |
| 11 | 18.00 | 30.00 | 17.33 | 34.67 | ○ | 0.50 |

HCS: Hydrophobic colloidal silica
X: Adhesive matrix showed poor stability. Transdermal patches showed release layer delamination or dimensional change in the reservoir matrix under accelerated stability storage conditions.
○: Adhesive matrix showed good stability. Transdermal patches showed little or no release layer delamination or dimensional change in the reservoir matrix under accelerated stability storage conditions.

Examples of Transdermal Patches with Hydrophobic Matrix Layers Laminated to a Drug-Free Adhesive Skin Contact Layer Transdermal patches were prepared including a hydrophobic matrix layer, also referred to as a drug reservoir layer; a drug-impermeable backing laminated to one surface of the hydrophobic matrix layer; and a release liner. In between the hydrophobic matrix layer and the release liner, there was a drug-free adhesive skin contact layer. The adhesive skin contact layer helps to control the rate of diffusion of methylphenidate from the transdermal patch, and is therefore also referred to as a rate-limiting layer.

The hydrophobic matrix layer contained methylphenidate as a hydrophobic drug in an amount of 18% by weight. The hydrophobic matrix layer also contained a combination of mineral oil (MO) and polyisobutylene (PIB) as a polymeric matrix. Specifically, the transdermal patch contained 18.00% methylphenidate and 20.00% hydrophobic colloidal silica in the drug reservoir layer and 2.00% hydrophobic colloidal silica and 0% methylphenidate in the adhesive skin contact layer, as seen in Table 2.

Table 2 presents two transdermal patch formulations. Each formulation is a bilayer composition, including a hydrophobic matrix layer, or drug reservoir layer, and an adhesive skin contact layer. The hydrophobic matrix layer is identical in each formulation. The rate limiting layers in the two formulations are identical in composition, but are coated to different thicknesses. In the formulations of Table 2, methylphenidate is present in the drug reservoir layer as a dispersed solid that is absorbed onto the surface of hydrophobic colloidal silica. In the formulations of Table 2, methylphenidate is not fully dissolved in the polymer matrix, and there are no visible drug crystals in the transdermal patch formulation.

TABLE 2

Transdermal Methylphenidate Formulations Containing an Adhesive Skin Contact Layer

|  | Prototype 1 | | Prototype 2 | |
| --- | --- | --- | --- | --- |
|  | % w/w | gsm | % w/w | gsm |
| Rate Limiting Layer | 33.33% | 30 | 53.85% | 70 |
| Methylphenidate | 0.00% | 0.00 | 0.00% | 0.00 |
| Hydrophobic Colloidal Silica NF (Aerosil R972 Pharma) | 2.00% | 0.60 | 2.00% | 1.40 |
| Light Mineral Oil NF (Drakeol 7) | 32.67% | 9.80 | 32.67% | 22.87 |
| Polyisobutylene Adhesive (Duro-Tak™ 87-613A) | 65.33% | 19.60 | 65.33% | 45.73 |
| Drug Reservoir Layer | 66.67% | 60 | 46.15% | 60 |
| Methylphenidate | 18.00% | 10.80 | 18.00% | 10.80 |
| Hydrophobic Colloidal Silica NF (Aerosil R972 Pharma) | 20.00% | 12.00 | 20.00% | 12.00 |
| Light Mineral Oil NF (Drakeol 7) | 20.67% | 12.40 | 20.67% | 12.40 |
| Polyisobutylene Adhesive (Duro-Tak™ 87-613A) | 41.33% | 24.80 | 41.33% | 24.80 |
| Combined Laminate | 100% | 90 | 100% | 130 |
| Methylphenidate | 12.00% | 10.80 | 8.31% | 10.80 |
| Hydrophobic Colloidal Silica NF (Aerosil R972 Pharma) | 14.00% | 12.60 | 10.31% | 13.40 |
| Light Mineral Oil NF (Drakeol 7) | 24.67% | 22.20 | 27.13% | 35.27 |
| Polyisobutylene Adhesive (Duro-Tak™ 87-613A) | 49.33% | 44.40 | 54.25% | 70.53 |

By adding another adhesive layer, which is the skin contact layer, to the hydrophobic matrix layer, the laminated hydrophobic matrix layer and adhesive skin contact layer in the finished dosage form showed good stability and showed little or no tendency to form oily layers or crystals at the interface between the skin contact layer and the release liner. Specifically, no crystals were observed at the interface between the skin contact layer and the release liner under room temperature and refrigerator storage conditions. However, at extreme storage conditions, such as storage in a freezer, e.g., at temperatures of −20° C., formation of crystals was sometimes observed.

In general, both the working examples of Table 1 and the examples of Table 2 were superior to the comparative examples of Table 1. The comparative examples of Table 1 had a greater tendency to form oily layers or crystals at the interface between the hydrophobic matrix layer, or drug reservoir layer, and the release liner than either the working examples of Table 1 or the examples of Table 2. Accordingly, inclusion of high levels of hydrophobic excipients, including hydrophobic colloidal silica, in the drug reservoir layer stabilizes the transdermal dosage form by reducing or preventing free diffusion of hydrophobic drugs through the hydrophobic matrix. Also, the examples of Table 2 were superior to both the comparative examples and working examples of Table 1. Accordingly, a drug-free skin-contacting adhesive layer containing a low level of hydrophobic excipients, including hydrophobic colloidal silica, further stabilizes the transdermal dosage form by reducing or preventing diffusion of hydrophobic drugs from the hydrophobic matrix to the interface with the release liner.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure and description are for illustrative purposes only and do not in any way limit the invention, which is defined only by the claims.

What is claimed is:

1. A hydrophobic patch for transdermal administration of a hydrophobic drug, comprising:
   a hydrophobic reservoir having a first surface and a second surface;
   a backing layer overlying said first surface, said backing layer being impermeable to said hydrophobic drug; and
   optionally a release sheet overlying said second surface;
   said hydrophobic reservoir comprising a hydrophobic matrix and said hydrophobic drug, said hydrophobic drug being homogeneously dispersed through said hydrophobic matrix,
   said hydrophobic matrix comprising:
      from about 6% to about 30% by weight of said reservoir of hydrophobic colloidal silica dispersed through said hydrophobic matrix; and
      a mixture of mineral oil and polyisobutylene in a weight ratio of said mineral oil to said polyisobutylene of between about 0.05:1 and about 1:1;
   wherein said hydrophobic colloidal silica adsorbs at least a portion of said hydrophobic drug.

2. The hydrophobic patch of claim 1, wherein said weight ratio of said mineral oil to said polyisobutylene is between about 0.087:1 and about 0.60:1.

3. The hydrophobic patch of claim 1, wherein said weight ratio of said mineral oil to said polyisobutylene is between about 0.25:1 and about 0.60:1.

4. The hydrophobic patch of claim 1, wherein said weight ratio of said mineral oil to said polyisobutylene is between about 0.30:1 and about 0.50:1.

5. The hydrophobic patch of claim 1, further comprising a release-controlling adhesive layer in contact with said second surface,
   with the proviso that if said release sheet is present, said release-controlling adhesive layer is between said hydrophobic reservoir and said release sheet.

6. The hydrophobic patch of claim 5, wherein said release-controlling adhesive layer comprises:
   from about 0.5% to about 5% by weight of said release-controlling adhesive layer of hydrophobic colloidal silica; and
   a mixture of mineral oil and polyisobutylene in a weight ratio of said mineral oil to said polyisobutylene of between about 0.05:1 and about 0.50:1.

7. The hydrophobic patch of claim 6, wherein said hydrophobic matrix in said hydrophobic reservoir comprises from about 8% to about 20% by weight of hydrophobic colloidal silica; and
   said release-controlling adhesive layer comprises from about 0.5% to about 4% by weight of hydrophobic colloidal silica.

8. The hydrophobic patch of claim 1, wherein said hydrophobic drug is a hydrophobic drug which is able to diffuse through said hydrophobic matrix.

9. The hydrophobic patch of claim 1, wherein said hydrophobic drug has a melting point of between 20° C. and 150° C.

10. The hydrophobic patch of claim 9, wherein said hydrophobic drug is methylphenidate, ibuprofen, clonidine, or scopalamine.

11. The hydrophobic patch of claim 9, wherein said hydrophobic drug is methylphenidate.

12. The hydrophobic patch of claim 1, wherein said hydrophobic colloidal silica has a mean particle size of between about 30 nm and about 150 nm.

13. The hydrophobic patch of claim 1, wherein said hydrophobic colloidal silica is colloidal silica which has been treated with a silane of formula I:

$$R_{(4-n)}SiX_n \qquad \text{I}$$

where R is a C1 to C20 alkyl or aromatic group, X is a hydrolysable group, and n is 1, 2, or 3.

14. The hydrophobic patch of claim 13, wherein X is —OH, —O$_2$CR$^1$, —Cl, —Br, —I, —OR$^1$, —COR$^1$, —NHR$^1$, or —NR$^1{}_2$, where R$^1$ is a C1 to C20 alkyl group.

15. The hydrophobic patch of claim 1, wherein the hydrophobic reservoir is a skin-contacting adhesive layer.

16. A hydrophobic patch for transdermal administration of a hydrophobic drug, wherein said hydrophobic drug is an oil or a drug having a melting point between about 20° C. and about 150° C., comprising:
   a hydrophobic reservoir comprising said hydrophobic drug, said reservoir having a first surface and a second surface;
   a backing layer overlying said first surface, said backing layer being impermeable to said hydrophobic drug; and optionally
   a release sheet overlying said second surface;
   said hydrophobic reservoir comprising said hydrophobic drug and a hydrophobic matrix, said hydrophobic matrix comprising:
      a mixture of mineral oil and polyisobutylene in a weight ratio of said mineral oil to said polyisobutylene of between about 0.05:1 and about 0.50:1; and
      an excipient or filler in an amount which is effective to adsorb said hydrophobic drug, thereby preventing said hydrophobic drug from forming a liquid or oily layer at the interface between said hydrophobic reservoir and said release sheet or said backing layer.

17. The hydrophobic patch of claim 16, wherein said hydrophobic drug and said excipient or filler are present in a weight ratio of between about 2:1 and about 0.9:1.

18. The hydrophobic patch of claim 16, wherein said excipient or filler is a hydrophobic filler.

19. The hydrophobic patch of claim 18, wherein said hydrophobic filler is hydrophobic colloidal silica.

20. The hydrophobic patch of claim 16, wherein said excipient or filler comprises at least one material selected from the group consisting of:
   hydrophobic colloidal silica in an amount of about 8% to about 30%;
   a combination of hydrophobic colloidal silica in an amount of about 1% to about 3% and titania in an amount of about 2%;
   neusilin (magnesium aluminometasilicate) in an amount of about 2% to about 5%;
   a combination of neusilin (magnesium aluminometasilicate) in an amount of about 2% to about 5% and at least one of magnesium stearate in an amount of about 2% to about 5% and polyethoxylated castor oil in an amount of about 2% to about 5%, and a mixture thereof;
   colloidal silica or dried colloidal silica in an amount of about 1% to about 10%;
   a combination of colloidal silica in an amount of about 1% to about 3% and at least one of neusilin in an amount of about 2%, magnesium stearate in an amount of about 1% to about 3%, disodium hydrogen phosphate in an amount of about 2% to about 5%, and polyethoxylated castor oil in an amount of about 2% to about 5%;
   disodium hydrogen phosphate in an amount of about 2% to about 5%;
   anhydrous calcium phosphate dibasic in an amount of from 5% to about 10%;
   a combination of anhydrous calcium phosphate dibasic in an amount of from 5% to about 10% and polyethoxylated castor oil in an amount of about 2% to about 5%;
   polyethoxylated castor oil in an amount of about 2% to about 5%;
   magnesium stearate in an amount of about 2% to about 5%;
   clays in an amount of about 5% by weight;
   up to 1% by weight of alpha-tocopherol; and
   from about 5% to about 20% of a cationic copolymer comprising dimethylaminoethyl methacrylate, butyl methacrylate, and methyl methacrylate;
   wherein all percentages are based on the weight of the hydrophobic reservoir.

21. A hydrophobic patch for transdermal administration of a hydrophobic drug, comprising:
   a skin-contacting adhesive layer;
   a drug reservoir layer comprising said hydrophobic drug, said drug reservoir layer having a first surface and a second surface, said first surface of said drug reservoir layer contacting said skin-contacting adhesive layer; and
   a backing layer overlying said second surface of said drug reservoir layer, said backing layer being impermeable to said hydrophobic drug;
   said skin-contacting adhesive layer comprising an adhesive matrix, said adhesive matrix comprising from about 0.5% to about 5% by weight of hydrophobic colloidal silica, and a mixture of polyisobutylene and mineral oil;
   wherein said hydrophobic colloidal silica prevents formation of a drug layer at the interface between said skin-contacting adhesive layer and said backing layer.

22. The hydrophobic patch of claim 21, wherein said drug reservoir layer comprises a hydrophobic matrix and said hydrophobic drug;
   said hydrophobic matrix comprising:
      from about 6% to about 30% by weight of said reservoir of hydrophobic colloidal silica dispersed through said hydrophobic matrix; and
      a mixture of mineral oil and polyisobutylene.

23. The hydrophobic patch of claim 1, wherein said hydrophobic colloidal silica has a specific surface area of between 90 m$^2$/g and 130 m$^2$/g.

24. The hydrophobic patch of claim 16, wherein said hydrophobic colloidal silica has a specific surface area of between 90 m$^2$/g and 130 m$^2$/g.

25. The hydrophobic patch of claim 21, wherein said hydrophobic colloidal silica has a specific surface area of between 90 m$^2$/g and 130 m$^2$/g.

* * * * *